United States Patent
Tojo et al.

(10) Patent No.: US 10,337,064 B2
(45) Date of Patent: Jul. 2, 2019

(54) METHOD FOR SCREENING AGENTS PROMOTING SKIN BARRIER FUNCTION AND METHOD FOR EVALUATING SKIN BARRIER FUNCTION TAKING EPIDERMAL SERINE RACEMASE AND/OR D-SERINE LEVEL AS INDICATOR

(71) Applicant: Shiseido Company, Ltd, Chuo-ku, Tokyo (JP)

(72) Inventors: Yosuke Tojo, Yokohama (JP); Masato Iino, Yokohama (JP); Chieko Mizumoto, Yokohama (JP); Yuzo Yoshida, Yokohama (JP); Yuko Matsuura, Yokohama (JP); Hisashi Mori, Toyama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/123,274

(22) PCT Filed: Mar. 5, 2015

(86) PCT No.: PCT/JP2015/056570
§ 371 (c)(1),
(2) Date: Sep. 2, 2016

(87) PCT Pub. No.: WO2015/133591
PCT Pub. Date: Sep. 11, 2015

(65) Prior Publication Data
US 2017/0073751 A1  Mar. 16, 2017

Related U.S. Application Data

(63) Continuation of application No. 14/477,213, filed on Sep. 4, 2014, now abandoned, which is a continuation of application No. PCT/JP2014/055680, filed on Mar. 5, 2014.

(30) Foreign Application Priority Data

Mar. 5, 2014 (JP) .................................. 2014-043073
Mar. 5, 2014 (WO) .................. PCT/JP2014/055680

(51) Int. Cl.
| | | |
|---|---|---|
| A61K 8/64 | (2006.01) | |
| C12N 9/90 | (2006.01) | |
| C12Q 1/6876 | (2018.01) | |
| G01N 33/50 | (2006.01) | |
| A61K 38/01 | (2006.01) | |
| A61K 36/9068 | (2006.01) | |
| A61K 36/28 | (2006.01) | |
| G01N 33/68 | (2006.01) | |
| C12Q 1/6883 | (2018.01) | |
| A61K 36/899 | (2006.01) | |
| A61K 8/97 | (2017.01) | |
| A61Q 19/00 | (2006.01) | |

(52) U.S. Cl.
CPC ............ *C12Q 1/6876* (2013.01); *A61K 8/645* (2013.01); *A61K 8/97* (2013.01); *A61K 36/28* (2013.01); *A61K 36/899* (2013.01); *A61K 36/9068* (2013.01); *A61K 38/011* (2013.01); *A61Q 19/00* (2013.01); *C12Q 1/6883* (2013.01); *G01N 33/5044* (2013.01); *G01N 33/6812* (2013.01); *A61K 2800/782* (2013.01); *C12Q 2600/136* (2013.01); *C12Q 2600/148* (2013.01); *C12Q 2600/158* (2013.01); *G01N 2333/968* (2013.01); *G01N 2333/99* (2013.01); *G01N 2800/20* (2013.01)

(58) Field of Classification Search
CPC ......... C12N 9/90; C12Q 1/533; C12Y 501/00
See application file for complete search history.

(56) References Cited

U.S. PATENT DOCUMENTS

| | | | |
|---|---|---|---|
| 2005/0100517 A1 | 5/2005 | Sanzgiri et al. | |
| 2007/0254021 A1 | 11/2007 | Scimeca et al. | |
| 2008/0003189 A1 | 1/2008 | Umishio et al. | |
| 2012/0148509 A1 | 6/2012 | Ashida et al. | |

FOREIGN PATENT DOCUMENTS

| | | |
|---|---|---|
| JP | 2012-092032 A | 5/2012 |
| TW | I337085 B | 2/2011 |
| TW | I372635 B | 9/2012 |
| TW | I381847 B | 1/2013 |
| WO | WO 2011/030903 A1 | 3/2011 |

OTHER PUBLICATIONS

Kelisema, 2012. Actvity ingredients for cosmetics. on the web at www.in-cosmetics.com/_novadocuments/243276?v= 636009890224430000.*
Inoue et al. Feb. 20, 2014; Localization of serine racemase and its role in the skin. J. Investigative Dermatology. 134:1618-1626.*
Dun et al. 2008; Serine racemase expression and D-serine content are developmentally regulated in neuronal ganglion cells of the retina. J. Neurochemistry. 104: 970-978.*
Paquet et al., "Racemization assessment in alkali treated dietary proteins using high-performance liquid chromatography," Nutrition Research, 1989, 9:1053-1066.

(Continued)

*Primary Examiner* — Karen Cochrane Carlson
(74) *Attorney, Agent, or Firm* — Foley & Lardner LLP (57) ABSTRACT

The purpose of the present invention is to develop a method for screening drugs having the effect of increasing skin barrier function in in vitro studies and to evaluate barrier function in the skin. Candidate drugs can be screened by using the activity and/or expression level of serine racemase as an indicator.

7 Claims, 5 Drawing Sheets
Specification includes a Sequence Listing.

(56) References Cited

OTHER PUBLICATIONS

Snyder et al., "D-Amino Acids as Putative Neurotransmitters: Focus on D-Serine," Neurochemical Research, 2000, 25(5):553-560.
Tojo, Yosuku, "Special Interview at the Research Front: Overlooked health functions of D-amino acids: Challenge its application in the skin science," Food Style Aug. 21, 2013, 17(8):8-11, with English translation.
Xia et al., "Characterization and localization of a human serine racemase," Molecular Brain Research, 2004, 125:96-104.
The 9$^{th}$ Annual Meeting of Amino Acid Research Society, Sep. 5, 2013, pp. 9, 17, 49.
Slides presented at 9$^{th}$ Annual Meeting of Amino Acid Research Society, Sep. 5, 2013.
The Japanese Society for Amino Acid Sciences (JSAAS2013), Nov. 2-3, 2013, pp. 81-82 and 87.
Slides presented at the Japanese Society for Amino Acid Sciences (JSAAS2013), Nov. 3, 2013.
Slides from seminar of possibility of metabolomics, Feb. 19, 2014.
Masaki, Hitoshi, "Experimental Protocol for Developing Ingredients in Functional Cosmetics," CMC Publishing, 2010, 214-216, with partial English translation.
Inoue et al., "Localization of Serine Racemase and Its Role in the Skin," Journal of Investigative Dermatology, Feb. 20, 2014, 134:1618-1626.
Tojo, Yosuke, "Free D-amino acids in human and foods as physiologically active molecules for skin," Amino San Kenkyu, Feb. 2014, 7(2):91-96.
Tojo, Yosuke, "Special interview at the Research Front: Overlooked health functions of D-amino acids: Challenge its application in the skin science," Food Style 21, Aug. 2013, 17(8):8-11.
Tojo, Yosuke, "Free D-amino acids in human and foods as physiologically active molecules for skin," Amino San Kenkyu, Feb. 2014, 7(2):91-96 with English translation.

\* cited by examiner

METHOD FOR SCREENING AGENTS PROMOTING SKIN BARRIER FUNCTION AND METHOD FOR EVALUATING SKIN BARRIER FUNCTION TAKING EPIDERMAL SERINE RACEMASE AND/OR D-SERINE LEVEL AS INDICATOR

TECHNICAL FIELD

The present invention relates to a method for screening a skin barrier function enhancing agent, and to a method for evaluating a skin barrier function for skin.

BACKGROUND ART

When skin barrier function is lost, water content in skin is also lost and invasion of exterior foreign matter occurs, creating a condition of sensitive and dry skin and skin roughening, and potentially relating to dermatitis and allergy. From the viewpoint of developing functional foods, cosmetics and pharmaceuticals, therefore, it is desirable to develop drugs that can increase skin barrier function. Factors for increasing skin barrier function include methods of increasing the amount of intercellular lipids or arranging their orientation, and drugs such as disclosed in PTL 1 have been developed that promote production of intercellular lipids.

Indicators for skin barrier function include transepidermal water loss (TEWL) and the degree of penetration into skin using an indicator substance such as a pigment. TEWL can be measured using an apparatus such as a Vapometer, but because measurement of moisture content is an unstable indicator easily affected by the measuring environment including atmospheric moisture content and air flow, as well as the body temperature, mental state and perspiration of the subject, it has been desired to devise methods allowing more stable evaluation of skin barrier function. When the degree of penetration of an indicator substance is to be used as the indicator of skin barrier function, the pigment or other indicator substance must be applied onto the skin, creating a significant burden on the skin.

In order to perform screening of drugs with effects of increasing skin barrier function from among numerous candidate drugs it is possible to use TEWL as the indicator of skin barrier function for in vivo experimentation, but this is unstable and significantly affected by the measuring environment, and it has been difficult to accomplish screening of drugs with an effect of increasing the physiological and structural skin barrier function from among numerous candidate drugs. On the other hand, such screening methods that have been considered include methods of using isolated skin to measure endogenous factors in skin that contribute to recovery and enhancement of barrier function, and evaluating the degree of recovery and enhancement of barrier function, but because of the lack of appropriate factors allowing convenient evaluation with small specimens, it has been a goal to identify such factors.

Almost all amino acids are known to be classified according to their enantiomeric absolute configuration, named as L-form and D-form, with the amino acids in living organisms being mainly the L-form, while D-amino acids have been thought to be found in a very limited number of biological components such as bacterial peptidoglycans. However, the results of recent research have demonstrated that various D-amino acids are to be found not only in microorganisms but also in plants and mammals, either in free form or as the amino acid residues composing proteins, and that they exhibit various types of physiological function. The firstly found free D-amino acids in mammals were D-serine and D-aspartic acid. D-serine is localized to the cerebrum and hippocampus and functions as an NMDA receptor co-agonist, and it has been found to play a role in excitatory neurotransmission control (NPL 1). Also, D-aspartic acid is localized in the testis and pineal body and has been found to contribute to control of hormone secretion. Results of recent research on D-amino acids have also further demonstrated that D-serine, D-aspartic acid, D-alanine, D-glutamic acid and D-proline are present in the dermis and epidermis, and are reduced with aging (NPL 2). D-serine is the D-amino acid with the highest content in the epidermis and stratum corneum, and while one role played by D-serine in the skin has been found to be alleviation of ultraviolet damage in dermal fibroblasts (PTL 2), its role in the epidermis where it is present in a higher content remains unknown.

Amino acid racemases are known as enzymes involved in production of D-amino acids, and they are classified into enzymes dependent on pyridoxalphosphoric acid (PLP) and racemases that do not require cofactors. Among reports that D-amino acids are present in eukaryotic cells including those of mammals it has been reported that PLP-dependent serine racemase is present in mammals (NPL 3), but it has not yet been confirmed whether or not aspartic acid racemase is present with racemase activity in mammals. Since D-serine is localized to the cerebrum and hippocampus, expression of serine racemase in the brains of mammals including humans has been confirmed, but there have been almost no reports of its expression in other tissues (NPL 3).

CITATION LIST

Patent Literature

[PTL 1] Japanese Unexamined Patent Publication No. 2012-92032
[PTL 2] WO2011/030903

Non-Patent Literature

[NPL 1] S. H. Snyder, et al., NeuroChem Res 25, 553 (2000)
[NPL 2] Y. Tojo, Food Style 21, 2013, August, (Vol. 17, No. 8)
[NPL 3] Molecular Brain Research, Vo 1. 125, pp. 96-104, 2004
[NPL 4] Overview of experimental protocols for development of functional cosmetic materials, CMC Publishing, 2010, p. 214-216

DISCLOSURE OF THE INVENTION

Problems to be Solved by the Invention

There has been interest in increasing skin barrier function by increasing intercellular lipid levels and ordering their arrangement. On the other hand, in order to enhance and repair skin barrier function, increasing the number of healthy stratum corneum layers is thought to be an effective approach in view of increasing physiological or structural skin barrier function. However, no drugs with such effects have been known, and as mentioned above, it has been difficult to discover such drugs by screening. Accordingly, it has been desired to develop a method for screening drugs having effects of increasing physiological or structural skin barrier function.

Means for Solving the Problems

As a result of diligent research on D-serine whose function in skin has not been known, the present inventors have discovered that D-serine contributes to skin barrier function. In addition, the present inventors have determined the influence of D-serine on cultured keratinocytes, and found that fillagrin, which has an important role on forming barrier function, as well as cornuline and repetin which relate to forming a cornified cell envelope are expressed. Based on these knowledge, it has become possible to provide a method for screening drugs having effects of increasing skin barrier function by using D-serine levels, as well as levels of expression and activity of serine racemase that produces D-serine from L-serine in keratinocytes as an indicator, and also to evaluate skin barrier function enhancement in a convenient and stable manner with low burden on subjects, whereupon the present invention has been completed. By using the screening method, it has become possible to screen for drugs that enhance skin barrier function.

Specifically, the present inventors have completed the following invention.

[1] A method for screening a skin barrier function enhancing agent, wherein an activity or expression level of serine racemase and/or D-serine level derived from keratinocytes is used as an indicator.

[2] The screening method according to [1], comprising:
adding a candidate drug to keratinocytes;
measuring the activity or expression level of serine racemase and/or the D-serine level derived from the keratinocytes; and determining the skin barrier function-enhancing effect of the candidate drug based on the expression level or activity of serine racemase and/or the D-serine level.

[3] The screening method according to [2], further comprising a step of inducing differentiation of the keratinocytes.

[4] The screening method according to [3], wherein the screening method is conducted in the differentiation-induced keratinocytes.

[5] The screening method according to any one of [1] to [4], wherein the measurement of the serine racemase expression level is carried out by measuring the amount of serine racemase mRNA or protein.

[6] The screening method according to any one of [1] to [4], wherein the measurement of serine racemase activity is carried out by measuring the substrate conversion efficiency or measuring the amount of D-amino acid product.

[7] A serine racemase activating agent comprising one or more substances selected from the group consisting of hydrolyzed oat protein, Lempuyang extract, *Elephantopus mollis* extract, pyridoxal phosphoric acid, and vitamin $B_6$s as an active ingredient, which is obtained by the screening method according to any one of [1] to [6].

[8] A method for evaluating the skin barrier function, wherein an activity or expression level of serine racemase and/or D-serine level from a skin sample isolated from human skin is used as an indicator. [9] The skin barrier function evaluation method according to [8], comprising:
measuring the activity or expression level of serine racemase and/or D-serine level in a skin sample isolated from a subject, and determining the skin barrier function of the subject from the activity or expression level of serine racemase and/or D-serine level.

[10] The skin barrier function evaluation method according to [8] or [9], wherein measurement of the serine racemase expression level is carried out by measuring the amounts of serine racemase mRNA or protein.

[11] The method according to [8] or [9], wherein the measurement of serine racemase activity is carried out by measuring the substrate conversion efficiency by serine racemase or the amount of D-amino acid product.

[12] A skin barrier function enhancing agent comprising one or more substances selected from the group consisting of hydrolyzed oat protein, Lempuyang extract, *Elephantopus mollis* extract, pyridoxal phosphoric acid, and vitamin $B_6$s, which is obtained by the screening method according to any one of [1] to [6].

[13] A method for enhancing skin barrier function, comprising administering one or more substances selected from the group consisting of hydrolyzed oat protein, Lempuyang extract, *Elephantopus mollis* extract, pyridoxal phosphoric acid, and vitamin $B_6$s.

[14] A method for activating serine racemase comprising administering one or more substances selected from the group consisting of hydrolyzed oat protein, Lempuyang extract, *Elephantopus mollis* extract, pyridoxal phosphate, and vitamin $B_6$s to a subject who is suffering from reduction of serine racemase activity.

[15] Use of hydrolyzed oat protein, Lempuyang extract, *Elephantopus mollis* extract, pyridoxal phosphoric acid, and vitamin $B_6$s for preparing a serine racemase activating agent.

[16] Use of hydrolyzed oat protein, Lempuyang extract, *Elephantopus mollis* extract, pyridoxal phosphoric acid, and vitamin $B_6$s for preparing a skin barrier enhancing agent.

Effect of the Invention

It is possible to select drugs that can improve or enhance skin barrier function by using the screening method of the invention. In addition, the skin barrier function evaluation method of the invention allows determining skin barrier function at the cellular level or tissue level, or at the biochemical level.

BEST MODE FOR CARRYING OUT THE INVENTION

The present invention relates to a method for screening skin barrier function enhancing agents, using an indicator, or a combination of two or more indicators among serine racemase expression level, activity and D-serine level in keratinocytes.

It is possible to obtain drugs having skin barrier function enhancing effects by using the screening method of the present invention. Here, "skin barrier function" means the function of the skin that retains moisture and prevents infiltration of foreign matter from the exterior, and the function is performed by the epidermis and especially by the stratum corneum. The skin barrier function can be measured by transepidermal water loss (TEWL), with higher moisture evaporation considered to be a lower skin barrier function. Enhancement of skin barrier function can be achieved, for example but not limited to, by increasing the number of layers of the stratum corneum, maturing the cornified envelope in the stratum corneum or increasing intercellular lipids, such as cholesterol and ceramide. Thus, while it is not intended to be constrained by theory, it is conjectured that applying a drug selected by the screening method of the invention onto skin can enhance serine racemase expression or activity, or increase D-serine levels, resulting in an effect of an increased number of layers of the stratum corneum, thereby enhancing the skin barrier function.

A candidate drug provided to the screening method of the invention can be any compounds, such as a compound obtained from a combinatorial library, or a mixture or extract. Examples of candidate drugs that may be used include libraries of compounds, mixtures, or extracts of food materials, cosmetic materials or pharmaceutical materials. The drugs considered to have skin barrier function enhancing effects according to the present invention can be applied in foods such as functional foods and nutritious foods, cosmetics, pharmaceuticals, or quasi drugs. Examples of cosmetics in which they may be applied include, for example but not limited to, cosmetic waters, creams, latexes, gels, essences, ointments, packs, bath additives, body soaps, shampoos, rinses, foundations and the like. More preferably, they are applied to cosmetics for sensitive skin, such as cosmetic waters, creams, latexes, essences and the like. A pharmaceutical or quasi drug may be in the form of any of various ointments or creams for transdermal administration, or in a form for oral administration.

In the screening method of the invention, serine racemase expression level or activity and/or D-serine level in keratinocytes, are used as an indicator. Use as an indicator means that the serine racemase expression level or activity, and/or D-serine level, is the factor to be considered. Thus, when a candidate drug is added, the screening method of the invention encompasses selection of a drug having a skin barrier function-enhancing effect based on serine racemase expression level or activity, and/or D-serine level as the judgment criteria.

Keratinocytes are cells constituting approximately 95% of the epidermis. Keratinocyte stem cells are present in the basal lamina of the epidermis in the body, and they migrate to the outside as they mature, thereby forming the stratum *spinosum*, granular layer and stratum corneum. Keratinocytes change their characteristics as they mature. The cells in the stratum *spinosum* or granular layer become flattened, lipids such as ceramides are released into the intercellular space, and then enucleation is occurred in the stratum *spinosum* of the outermost layer. This maturation process can be considered differentiation of keratinocytes. The enucleated cells lose their cytomorphology and become superposed, thereby forming the stratum corneum, and are eventually shed off as scales from the outermost layer.

The cultured keratinocytes to be used for the invention may be cells obtained from the epidermal basal lamina, stratum *spinosum*, granular layer or stratum corneum, or cells that have been induced to differentiate from stem cells such as skin epithelial stem cells or pluripotent stem cells, for example, ES cells, iPS cells, EG cells, etc. Cells obtained from the epidermis and cultured may be primary cultured cells, subcultured cells, or even cancerized or immortalized cells. The cultured keratinocytes to be used for the invention may also be an established keratinocyte line derived from a human or animal. Such keratinocyte cell lines can be obtained from authorized institutions or distributors.

The cultured product may refer to the desired cells alone, or it may also contain other cells or it may be composed of the cells and the culture medium. Thus, cultured keratinocytes may refer to the keratinocytes alone, or to a combination of the keratinocytes with other cells, or to culture medium with the keratinocytes alone or with the keratinocytes and other cells. Such a cultured product may include a monolayer cultured product, mixed cultured product or three-dimensional cultured product. The culture medium in which the keratinocytes are cultured may include any desired culture medium so long as it allows to culture keratinocytes, for example not limited to, HuMedia-KB2 (Kurabo Industries, Ltd.) or Keratinocyte-SFM (Invitrogen Corp.) medium with addition of various additives may be used. The culturing conditions will usually be at 37° C. in the presence of 5% $CO_2$, with variation in a range that permits proliferation of keratinocytes. The culture medium is preferably in an L-serine-enriched state, from the viewpoint of using D-serine abundance as an index of serine racemase activity. In most cases, D-amino acids will not be intentionally added to the culture medium, and the abundance of L-serine with respect to D-serine in the culture medium will be at least 1.1-fold, more preferably 10-fold and even more preferably 50-fold or greater. For example, culture medium (KGM culture medium) obtained by adding an HuMedia-KG proliferating additive set to HuMedia-KB2 (Kurabo Industries, Ltd.) has the 100-fold or greater abundance of L-serine with respect to D-serine.

The keratinocytes cultured product has been cultured after seeding, and the keratinocytes cultured product being about 50% confluency to confluent can be subjected to experiment. The confluency is preferably 70% or greater and even more preferably 80% or greater, from the viewpoint of inducing differentiation. The process for adding a candidate drug to the cultured keratinocytes may involve exchanging the culture medium for the cultured keratinocytes with a culture medium containing the candidate drug, or adding the candidate drug, either directly or as a diluted solution, to the cultured product containing the keratinocytes and the culture medium.

Serine racemase is a racemase that is dependent on pyridoxal-5' phosphate (PLP), a coenzyme of vitamin B6. While it is not intended to be constrained by theory, serine racemase is an enzyme capable of conversion between L-serine and D-serine via production of an anionic intermediate, by withdrawal of the α-hydrogen from serine. In the conversion reaction between L-serine and D-serine, there is no change in enthalpy before and after the reaction, and the reaction is driven by entropy. Therefore, L-serine and D-serine are equivalent in the equilibrium state. Since the abundance of L-serine is greater than D-serine in the body, the presence of serine racemase converts L-serine in the body to D-serine. Since the L-form is usually more abundant in culture medium even under culturing conditions, the presence of serine racemase similarly converts L-serine to D-serine. According to the invention, the racemase can be identical to the racemase found to be expressed in the brain according to NPL 3, or a homolog or ortholog thereof. Thus, it can be amplified by a primer pair used in that publication, and is detectable by the racemase antibody described in the same publication. Serine racemase can be identified by a person skilled in the art according to animal species, from the web site of an authorized institution such as NCBI.

According to one aspect of the invention, serine racemase activity in keratinocytes can be used as an indicator for evaluation of skin barrier function or for screening of skin barrier function enhancing agents. Serine racemase activity can generally be based on the amount of D-serine produced by conversion of L-serine in the culture medium, when a substance acting as the substrate for the enzyme is not added, or it may be based on the total amount of other D-amino acids including D-serine. Also, addition of a substance other than serine that can serve as a substrate for serine racemase may be carried out to measure the amount of product or measure the conversion efficiency, based on conversion of the additive. Since serine racemase converts excess optical isomer to the other optical isomers until the D-form and L-form ratio become 50:50, it is of course possible to add the D-form for activity measurement. In this case, evaluation of enzyme activity can be accomplished even by measuring the increase in L-serine produced by conversion. If a derivative of cycloserine or serine (such as the N-methylated form, acetylated form or phosphorylated form) is also added, it is possible to evaluate the enzyme activity by examining the conversion efficiency to the corresponding optical isomer. When serine racemase activity is to be measured based on the D-serine level, it may be determined by the abundance of D-serine in a skin sample isolated from a subject, or in cultured keratinocytes, i.e. in a culture medium, cells or both, or it may be determined by an enzymatic parameter determined based on the change in the abundance of D-serine in a skin sample or in cultured keratinocytes. This method is applicable to all of the aforementioned substances that can act as enzyme substrates. The enzymatic parameter representing serine racemase enzyme activity may be obtained by determining the $V_{max}$ or $K_m$ values.

According to another aspect of the present invention, the D-serine level in keratinocytes can be used as an indicator for evaluation of skin barrier function or for screening of skin barrier function enhancing agents. The D-serine level may be measured in a skin sample isolated from a subject, or in cultured keratinocytes, i.e. in a culture medium, cells or both. The method of measuring the D-serine level may be carried out using a known method. For example, it may be carried out by an HPLC method using an optical isomer separating column, or a gas chromatography, electrophoresis or enzyme method. When measurement of the serine racemase activity is carried out by measuring the D-serine level, L-serine may be added to the cultured keratinocytes to increase the D-serine level. When serine racemase catalyzes conversion reaction between L-serine and D-serine, the enthalpy before and after the reaction does not change, and the reaction is driven by entropy. Therefore addition of L-serine can increase the D-serine level in proportion to the serine racemase activity, and therefore measurement of the D-serine level becomes easier.

According to another aspect, serine racemase expression level can be used as an indicator for evaluation of skin barrier function or for screening of skin barrier function enhancing agents. The serine racemase expression level can be determined by measuring serine racemase protein by an immunological method using anti-serine racemase antibody. The immunological method can be carried out by Western blotting, fluorescent immunostaining or ELISA. The anti-serine racemase antibody used may be monoclonal antibody or polyclonal antibody, and it may be antibody collected by immunizing an experimental animal such as a rabbit or mouse with serine racemase protein or antigen peptide.

It can also be accomplished by determining the serine racemase expression level based on the amount of serine racemase mRNA in cells. The mRNA may be measured by any desired method, and for example, it can be measured based on a quantitative PCR method. A quantitative PCR method is usually conducted as follows, with the understanding that this is not limitative. The mRNA is extracted from collected cells, and cDNA is prepared using polyT primer and reverse transcriptase. The prepared cDNA may be subjected to the SYBR green method or fluorogenic probe method to quantify the amount of mRNA in the cells.

More specifically, the screening method of the invention may comprise the following steps:
adding a candidate drug to keratinocytes,
measuring the expression level or activity of serine racemase and/or the D-serine level in keratinocytes, and
determining the skin barrier function-enhancing effect of the candidate drug based on the expression level or activity of serine racemase and/or the D-serine level. The screening method of the invention may further comprise a step of inducing differentiation of keratinocytes.

The differentiation inducing step is carried out by subjecting keratinocytes to differentiation-inducing stimulation. Subjecting keratinocytes to differentiation-inducing stimulation results in cellular flattening, increase in intracellular fibers or granules, indistinct intercellular spaces, superpositioning (especially with monolayer cultures), and finally resulting in the morphological change of enucleation, or changes in cells that result in production of or changes in proteins such as keratin 1, keratin 10, involucrin or transglutaminase activation (see Nippi Kaishi, 90(12), 1089-1101, http://drmtl.org/data/090121089.pdf, Drug News Perspect 2004, 17(2) p 117). The differentiation-inducing stimulation may be any desired stimulation that can produce the aforementioned differentiation of keratinocytes, and may include, for example, stimulation of calcium ion that increases the calcium ion concentration, stimulation with phorbol-12-myristate-13-acetate (Hawley-Nelson P, Stanley J R et al, Exp Cell Res, 137: 155-167, 1982), physical stimulation by voltage or gas phase exposure, or stimulation with a biological solution. For stimulation with calcium ion, a calcium salt or its diluted solution may be added to a concentration of 0.1 mM to 10 mM as the final concentration of calcium ion, or the culture medium may be exchanged with medium already adjusted to a final concentration of calcium ion. The calcium salt used includes, for example, calcium chloride, calcium hydrogencarbonate, calcium carbonate, calcium nitrate or calcium acetate, etc. The upper limit for the final calcium ion concentration is preferably 5 mM and even more preferably 2 mM, from the viewpoint of not adversely affecting the cell culture. From the viewpoint of promoting the induced differentiation, the lower limit for the concentration is preferably 0.5 mM and more preferably 1.0 mM.

The differentiation-inducing step and the candidate drug addition step may be carried out simultaneously, the candidate drug addition step may be carried out after the differentiation-inducing step, or conversely the differentiation-inducing step may be carried out after the candidate drug addition step. While it is not intended to be limited to theory, the timing for inducing differentiation and adding candidate drugs can be varied depending on the action mechanism desired for the candidate drug. For example, from the viewpoint of examining antagonism of drugs with differentiation-inducing stimulation substances, the addition step is preferably carried out either simultaneously with or before the stimulation step. Also, from the viewpoint of promoting or inhibiting cellular changes (morphological changes, and expression of various intracellular factors) after differentiation has been induced, the addition step is preferably carried out simultaneously with or after the stimulating step, and from the viewpoint of illuminating mechanisms such as exploring mechanisms such as pre-blocking of receptors on which differentiation-inducing stimulation acts, the stimulating step is preferably carried out after the addition step. When the candidate drug addition step and the differentiation-inducing stimulation step are not carried out simultaneously, a cell culturing step of several minutes to several hours may be included between the addition step and the stimulation step.

After differentiation-inducing stimulation and candidate drug addition, a cell culturing step may be further included before the step of measuring the serine racemase expression level or activity and/or the D-serine level. The period for the cell culturing step can be selected as desired depending on the type and concentration of the differentiation-inducing agent used and the type of keratinocytes, and culturing may be conducted for 6 hours to 1 week, for example. From the viewpoint of adequately expressing serine racemase, the minimum culturing period is preferably 12 hours and more preferably 1 day. On the other hand, the maximum culturing period cannot be specified since it will differ depending on the culturing method, such as monolayer culturing, multi-layered culturing or three-dimensional culturing, but from the viewpoint of maintaining normal cell culturing conditions it is preferably no longer than one week and more preferably no longer than 3 days, for monolayer culturing.

The screening method of the invention may further include a damage-inducing step. The damage-inducing step may be inducement of damage by physical or chemical stimulation of the cultured keratinocytes, such as addition of a radical source such as ultraviolet irradiation or an oxidizing agent, addition of a surfactant, or exchange with oligotrophic medium. The keratinocytes that have been damaged by the damage-inducing step may be expected to have reduced serine racemase expression. Thus, in a screening method in which a damage-inducing step is carried out after the candidate drug addition step, if reduction in racemase expression level or racemase activity and/or D-serine level is found to be suppressed, the candidate drug can be used as a preventive drug against damage to skin barrier function. On the other hand, in a screening method in which a candidate drug addition step is carried out after a damage-inducing step, if reduced racemase expression level or racemase activity and/or D-serine level is found to be increased, the candidate drug can be used as a restoring, ameliorating or curative agent for skin barrier function. In a screening method where damage is not induced, a candidate drug that increases racemase expression level or racemase activity, and/or D-serine level, can be considered to be an enhancer of skin barrier function.

As a result of carrying out the screening method of the present invention which uses the expression level of serine racemase as an indicator, hydrolyzed oat protein, Lempuyang extract, and *Elephantopus mollis* extract can be selected as an agent enhancing the expression level of serine racemase in keratinocytes. When the expression level of serine racemase is increased, the serine racemase activity is also enhanced, and D-serine amount in stratum corneum is increased, thereby skin barrier function is enhanced. Thus, these substances can be referred to as a serine racemase expression enhancing agent, serine racemase activating agent or skin barrier enhancing agent. A drug screened by means of the screening method according to the present invention is not limited to extract derived from Lempuyang and *Elephantopus mollis*, and extract derived from related species has also the skin barrier function enhancing effect in a similar way. Therefore, the serine racemase expression enhancing agent, the serine racemase activating agent, or the skin barrier function enhancing agent of the present invention include extract of a plant belonging to the genus *Zingiber* of Zingiberaceae family and a plant belonging to the *Elephamtopus* genus of Compositae family. Therefore, a cosmetic product exerting skin barrier function enhancing effect can be prepared by containing these substances in a cosmetic product.

In addition, as a result of carrying out the screening method of the present invention, which uses the serine racemase activity as an indicator, for a cosmetic material library, pyridoxal phosphoric acid (PLP: Activated vitamin B6) can be screened in keratinocytes. When the serine racemase activity is enhanced, D-serine amount in stratum corneum is increased, and thereby the skin barrier function is enhanced. Therefore, pyridoxal phosphoric acid can be referred to as a serine racemase activating agent or skin barrier enhancing agent.

The hydrolyzed oat protein used in the present invention is a hydrolyzate of protein obtained from oat (*Avena sativa* L.). While the protein of oat is extracted, for example, from seeds, leaves, roots, and from bran, the seeds are particularly preferred. The oat, which was immediately dried and ground after harvest, are preferred. It may be dried under the sun, or may be dried by using a drying machine that is normally used. The protein is hydrolyzed by the acid or enzyme treatment in the process of extraction or after extraction. Oats is a plant that is grown for food from West Asia to Europe and North America. The extraction solvent used in the present invention can be any solvent usually used for extraction. In particular, an organic solvent including alcohols such as methanol, ethanol, water-containing alcohols, acetone, ethyl acetate ester can be used for extraction alone or in combination. It is possible to perform the extraction with water.

The amount of the hydrolyzed oat protein of the present invention can be arbitrarily selected by a person skilled in the art within the scope exerting an effect. For example, the amount of the extract constitutes, as a dry composition, 0.0005-20.0 wt % of the total amount of the external formula The upper limit of the amount is preferably less than 10 wt % by weight or less, and more preferably 5 wt % or less from the viewpoint of exerting an effect and preparing a formulation. The lower limit of the amount is preferably 0.0001 wt % or more, more preferably 0.0005 wt % or more in view of exerting a sufficient skin barrier function enhancing effect.

Among plants belonging to the genus *Zingiber* of Zingiberaceae family, Lempuyang (*Zingiber aromaticum* Mal.) is preferable. Lempuyang is a plant growing dry grassland and pasture in particular in Indonesia. The extract used in the present invention is prepared by immersing foliage, stem including rhizomes, fruits, etc., of the plant and the whole plant in an extract solvent, optionally heating the mixture to reflux, then being subjected to filtration and concentration. The extraction solvent used in the present invention can be any solvent usually used for extraction. In particular, an organic solvent including alcohols such as methanol, ethanol, water-containing alcohols, acetone, ethyl acetate ester can be used for extraction alone or in combination. It is possible to perform the extraction with water.

The amount of the extract of a plant belonging to the genus *Zingiber* of Zingiberaceae family can be arbitrarily selected by a person skilled in the art within the scope exerting an effect. For example, the amount of the extract constitutes, as a dry composition, 0.0005-20.0 wt % of the total amount of the external formula The upper limit of the amount is preferably less than 10 wt % by weight or less, and more preferably 5 wt % or less from the viewpoint of exerting an effect and preparing a formulation. The lower limit of the amount is preferably 0.0001 wt % or more, more preferably 0.0005% wt % or more in view of exerting a sufficient skin barrier function enhancing effect.

Among a plant belonging to the genus *Elephamtopus* of Compositae family, *Elephantopus mollis* is preferable. *Elephantopus mollis* is an indigenous plant in Venezuela of South America, and has been widely naturalized in tropical Asia. The extract of a plant belonging to the genus *Elephamtopus* of Compositae family is prepared by immersing Leaves, stems, flowers, bark, seeds or fruit, etc., of the plant and the whole plant in an extract solvent, optionally heating the mixture to reflux, then being subjected to filtration and concentration. The extraction solvent used in the present invention can be any solvent usually used for extraction. In particular, an organic solvent including alcohols such as methanol, ethanol, water-containing alcohols, acetone, ethyl acetate ester can be used for extraction alone or in combination. It is possible to perform the extraction with water.

The amount of the extract of a plant belonging to the genus *Elephamtopus* of Compositae family can be arbitrarily selected by a person skilled in the art within the scope exerting an effect. For example, the amount of the extract constitutes, as a dry composition, 0.0005-20.0 wt % of the total amount of the external formula The upper limit of the amount is preferably less than 10 wt % by weight or less, and more preferably 5 wt % or less from the viewpoint of exerting an effect and preparing a formulation. The lower limit of the amount is preferably 0.0001 wt % or more, more preferably 0.0005% wt % or more in view of exerting a sufficient skin barrier function enhancing effect.

Pyridoxal phosphoric acid (PLP) used in the present invention is a substance used as a coenzyme of serine racemase. Pyridoxal phosphoric acid is an activated form of pyridoxal, which is known as vitamin $B_6$s. Without wishing to be bound by any theory, it is believed that pyridoxal phosphoric acid can increase the activity of serine racemase as a coenzyme, and then D-serine produced by the activity of serine racemase has an effect on keratinocytes. Thereby the expression of a group of genes relating to skin barrier function, such as filaggrin, cornuline and repetin is enhanced, and thus skin barrier function is enhanced. Vitamin $B_6$s, which are known as ingredients to be composed in cosmetic products, comprises pyridoxine, pyridoxamine, in addition to pyridoxal. Since Vitamin B6s are water-soluble, dermal administration thereof may cause a problem in absorption rate or stability. In order to improve dermal absorption, vitamin B6 derivative wherein lipophilicity is increased are known. Thus, a vitamin $B_6$ derivative, such as pyridoxine tris-hexyldecanoate, pyridoxine tripalmitate, pyridoxine dipalmitate, pyridoxine dicaprylate, are also incorporated in vitamin B6s. Pyridoxine cyclic phosphate and pyridoxine hydrochloride are also known for improving stability. Not only pyridoxal phosphoric acid, but also vitamin $B_6$s are also used as a serine racemase activating agent or dermal function enhancing agent. The content of these compounds are, for example, 0.000001-10 w/w %. The upper limit of the content is preferably less than 10 w/w %, further preferably less than 1 w/w %, in term of the formulation and effect. The lower limit is preferably more than 0.000001 w/w %, more preferably more than 0.00001 w/w % in term of exerting a sufficient skin barrier function enhancing effect.

In a step of determining the skin barrier function-enhancing function of a candidate drug based on serine racemase expression level or activity, or D-serine level, it is possible to determine it based on the measured serine racemase expression level or activity and/or D-serine level using a preset table showing the relationship between expression level or activity and/or D-serine level and barrier function-enhancing function. Such a table can be prepared using racemase expression level or activity and/or D-serine level measured by a similar experiment without the candidate drug, as a control, or using racemase expression level or activity and/or D-serine level measured by a similar experiment using a control drug known to increase serine racemase expression level or activity and/or D-serine level. According to a different aspect, the skin barrier function-enhancing action of a candidate drug can be determined by setting a predetermined threshold value based on comparison with a control, and determining whether or not the effect is higher than the threshold value by a statistically significant difference. A person skilled in the art can appropriately set the threshold value according to the skin barrier function-enhancing effect that is desired. Such a threshold value may be a threshold value set to an arbitrary factor with respect to serine racemase expression level or activity and/or D-serine level for a control where the drug has not been added, and for example, the value may be set to a factor of 1.1, for example, by a statistically significant difference and marginal significant difference. A statistically significant difference is $p<0.05$, and a marginal significant difference is $p<0.1$. Also, according to yet a different mode, it may be determined that a skin barrier function-enhancing effect is exhibited in the case of high expression level or activity compared to the racemase expression level or activity and/or D-serine level measured by conducting a similar experiment without the candidate drug, as a control, in which case it can be determined that higher expression level or activity and/or D-serine level is a greater skin barrier function-enhancing effect.

According to yet another aspect, the invention relates to a method of evaluating, judging and discriminating skin barrier function using serine racemase expression level or activity and/or D-serine level as an indicator. Such evaluation, judgment or discrimination can be made by measuring D-serine content, serine racemase activity or serine racemase expression level for a skin sample such as a stratum corneum sample obtained by tape stripping, for example, from a subject. The method of evaluating, judging or discriminating skin barrier function will usually be carried out by measuring TEWL using a Vapometer. However, TEWL is dependent on the state of the skin and its numerical values vary depending on rinsing and abrasion, while in skin disease patients there is no definite correlation between the numerical values and skin health. The evaluation, judgment and discrimination method of the invention uses serine racemase activity or expression level and/or D-serine level as an indicator to allow measurement of the original cellular-level skin barrier function of skin. Also, since the evaluation method of the invention determines the normalcy of skin barrier function on the cellular level, it allows prediction of future skin barrier function rather than current skin barrier function. The evaluation, judgment or discrimination of skin barrier function can be made using a table or threshold value representing the relationship between a previously set serine racemase expression level or activity and/or D-serine level, and barrier function-enhancing effect. Such a table or threshold value can be set based on expression level or activity and/or D-serine level obtained for a skin sample obtained and isolated from subject groups with healthy skin, subject groups with roughened skin, and from age-classified subject groups.

It has been found that the expression of some genes is increased by adding D-serine to cultured cells. Among them, it has been found that filaggrin, which has an important role on forming a barrier function, and cornuline and reptin, which relate to forming cornified cell envelope (CE), are increasingly expressed. Without wishing to be bound by any theory, it is believed that a serine racemase activating or expression enhancing agent, which is screed by the present invention, could enhance D-serine content in keratinocytes, and that D-serine enhances the expression of proteins, which relate to barrier function, thereby skin barrier function is enhanced. Therefore, D-serine can be used as a skin barrier function enhancing agent. In addition, D-serine is also referred to as an expression enhancing agent of filaggrin, cornuline and repetin, or is referred to as a keratinization promotion agent.

Filaggrin is a basic protein which is in rich of histidine, arginine, serine, glycine, glutamic acid, etc., and has a function of depositing on keratin fibers and then aggregating them. Thus, since keratin fibers in keratinocytes are aggregated, a whole cell is flattened, thereby a whole cell forms horny layer from granular layer, and then is keratinized. Filaggrin is expressed as a precursor named profilaggrin in granular cells of epidermis. When the granular cells are keratinized, pro-filaggrin is subjected to an action of proteinase, and thus is degraded into filaggrin. The decrease in filaggrin is thought to be a major factor of developing an ichthyotic disease or atopic dermatitis, and skin barrier function is remarkably decreased in these diseases.

Cornuline and repetin are proteins which composing cornified cell envelope which is lining on a cellular membrane of keratinocytes. Cornuline and repetin are expressed from genes present on 1q21 chromosome position at the final stage of cornification, in a similar way of involucrin, loricrin, etc., which are the components of cornified cell envelope. Proteins composing cornified cell envelope participate in skin barrier function along with keratin which is aggregated by the action of filaggrin.

A skin barrier function enhancing agent or serine racemase activating agent screened by the screening method of the present invention can be added to a cosmetic product or to a medicament. Such a cosmetic product is used for an object who has a decreased skin barrier function, such as an object who is suffering from a condition, such as atopic dermatitis, ichthyotic disease, psoriasis, skin problem. In addition, when the skin barrier function enhancing agent or serine racemase activating agent is added to a medicament, the medicament can be used as a pharmaceutical composition for treating atopic dermatitis, ichthyotic disease, psoriasis, etc.

The present invention will now be explained in greater detail by the following examples. However, the invention is in no way limited by the examples.

EXAMPLES

Example 1

Figure 1:
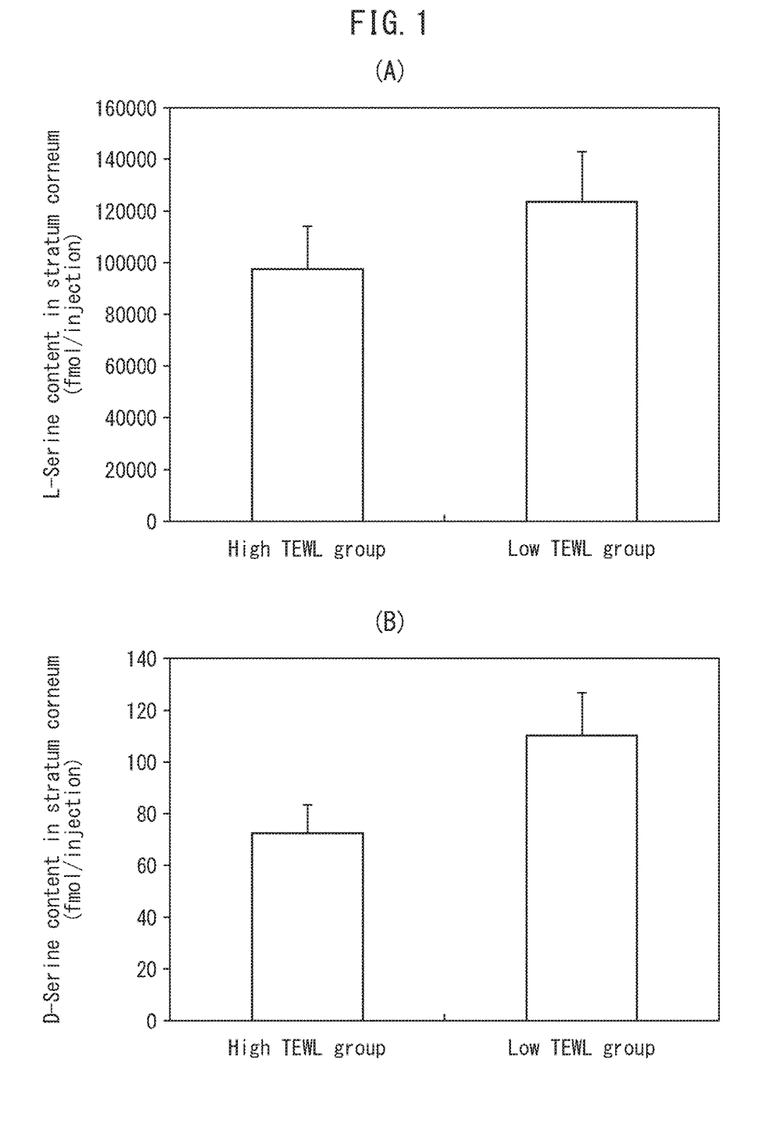
FIG. 1A shows a comparison of free L-serine levels in skin in a high-TEWL group and a low-TEWL group.
FIG. 1B shows a comparison of free D-serine levels in skin in a high-TEWL group and a low-TEWL group.

Verification of Relationship Between D-serine Content and Barrier Function in Stratum Corneum The subjects were 57 volunteers having healthy test sites, and the test sites wetted by rinsing after cleaning by a prescribed method were allowed to stand for 30 minutes at constant temperature, constant humidity conditions (room temperature: 22° C., humidity: 45%). Next, the transepidermal water loss (TEWL) was measured with a Vapometer (Delfin Co.). Measurement was performed 3 times and the average value was subsequently used for analysis. Next, the stratum corneum at the TEWL-measured site was stripped twice using adhesive tape and the second was used for extraction of amino acids in a 95% methanol aqueous solution. The optical isomers of the extracted amino acids were analyzed by a reported method (reference: Yurika Miyoshi et al., Journal of Chromatography B, 877 (2009) 2506-2512). The results are summarized below. The extracted amino acids were subjected to fluorescent derivatization with 4-fluoro-7-nitro-2,1,3-benzooxadiazole (NBD-F) in a borate buffer (pH 8.0). After this derivatization, pH of the solution was adjusted to acidic conditions by adding trifluoroacetic acid. The derivatives were subjected two-dimensional Micro HPLC (Shiseido Corp.). For the first dimension there was used a micro monolithic ODS column (inner diameter: 0.53 mm, full lengths: 500, 750, 1000 mm, Shiseido Corp.), and for the second dimension there was used an optical resolution enantio-selective column (inner diameter: 1.5 mm, full length: 250 mm, mobile phase conditions were optimized for each amino acid). The NBD-amino acids were detected by fluorescence at 530 nm (excitation wavelength of 470 nm). The results are shown in Table 1 and FIG. 1.

TABLE 1

| | | High TEWL group (=low barrier group) | | | Low TEWL group (=high barrier group) | |
|---|---|---|---|---|---|---|
| n | TEWL | D-Ser (fmol/ injection) | L-Ser (fmol/ injection) | TEWL | D-Ser (fmol/ injection) | L-Ser (fmol/ injection) |
| Mean | 10 | 69 | 97633 | 6 | 106 | 123496 |
| SE | 0.23 | 11 | 16503 | 0.15 | 16 | 19546 |
| p-value in student's t-test | | | | | 0.013 | 0.146 |

In order to verify the relationship between D-serine (D-Ser) content and skin barrier function in the stratum corneum, the subjects were ordered according to TEWL value, and the D-serine contents in the stratum corneum were compared between the top 17 (inferior barrier function group) and bottom 17 (superior barrier function group). The significant difference between the two groups was verified by a non-paired Student's t-test. The results demonstrated that humans with high skin barrier function had significantly high D-serine contents. On the other hand, results of comparison for L-serine indicated a tendency toward lower L-serine content in the inferior barrier function group and higher L-serine content in the superior barrier function group, although the difference was not significant. Thus, it may be concluded that the high D-serine content in the superior barrier function group was not due to the amount of L-serine as the precursor, but rather to racemase expression and activity.

Example 2

Variation in D-serine Content with Induced Differentiation of Keratinocytes

Cell Culturing and Drug Preparation

Normal human keratinocytes were seeded in a 24 well multiplate to a cell density of $2.5 \times 10^4$ cells/well, and cultured in KGM culture medium (Kurabo Industries, Ltd.) under conditions of 37° C., 5% $CO_2$. After 3 days, the medium was exchanged with KGM culture medium to which 1.8 mM calcium chloride and 10 mM L-serine had been added (test group), or KGM culture medium to which 10 mM L-serine alone had been added (control group), and culturing was continued for another 2 days.

HPLC Sample Preparation and Free D-serine Analysis by HPLC.

Figure 2:
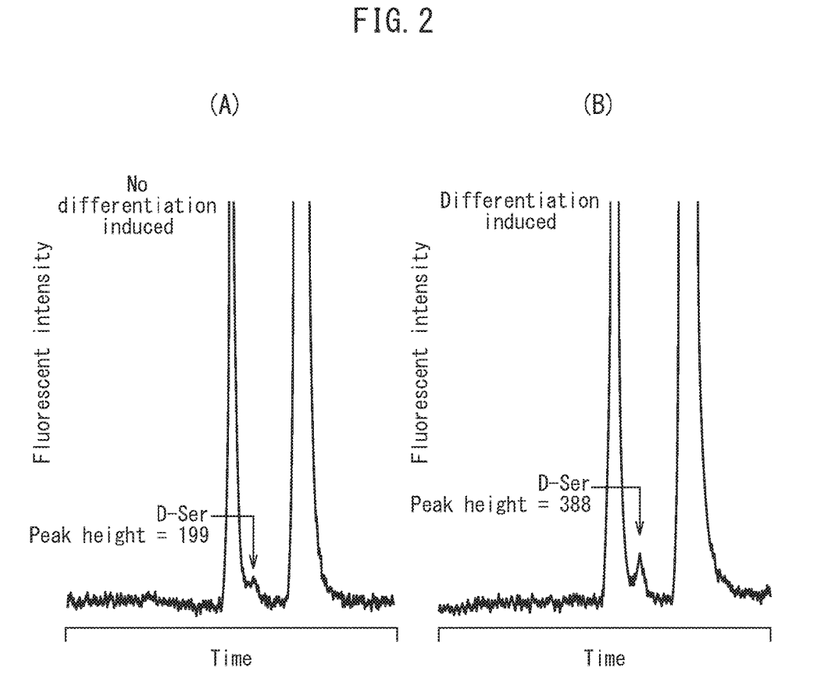
FIG. 2 is chromatograms for detection of intracellular D-serine before and after differentiation-inducing stimulation of cultured keratinocytes.

After rinsing cells with PBS, 500 μL of a 5% trichloroacetic acid aqueous solution was added, the cells were thoroughly dispersed and recovered, and ultrasonic treatment was performed for 30 minutes on ice, after which centrifugal separation was performed to obtain a supernatant. The amino acids in the supernatant were extracted by addition of a 20-fold amount of methanol. The optical isomers of the extracted amino acids were analyzed by a reported method (reference: Yurika Miyoshi et al., Journal of Chromatography B, 877 (2009) 2506-2512). The results are summarized below. The extracted amino acids were subjected to fluorescent derivatization with 4-fluoro-7-nitro-2,1,3-benzooxadiazole (NBD-F) in a borate buffer (pH 8.0). After this derivatization, pH of the solution was adjusted to acidic conditions by adding trifluoroacetic acid. The derivatives were subjected to two-dimensional Micro HPLC (Shiseido Corp.). For the first dimension there was used a micro monolithic ODS column (inner diameter: 0.53 mm, full length: 750 mm, Shiseido Corp.), and for the second dimensional optical resolution, there was used an optical resolution enantio-selective column inner diameter: 1.5 mm, full length: 250 mm, mobile phase conditions were optimized for each amino acid). The NBD-amino acids were detected by fluorescence at 530 nm (excitation wavelength of 470 nm). The results for the test group and control group are shown in FIG. 2.

Example 3

Screening of Candidate Drugs

Cell Culturing and Drug Preparation

Normal human keratinocytes were seeded in a 24 well multiplate to a cell density of $2.5 \times 10^4$ cells/well, and cultured in KGM culture medium (Kurabo Industries, Ltd.) under conditions of 37° C., 5% $CO_2$. After 3 days, the medium was exchanged with KGM culture medium containing 1.8 mM calcium chloride, 10 mM L-serine and the candidate drug diluted solution, and culturing was continued for another 2 days. Seven drugs were used as candidate drugs, of which one was a 0.5% hydrolyzed oat protein solution.

HPLC Sample Preparation and Free D-serine Analysis by HPLC.

Figure 3:
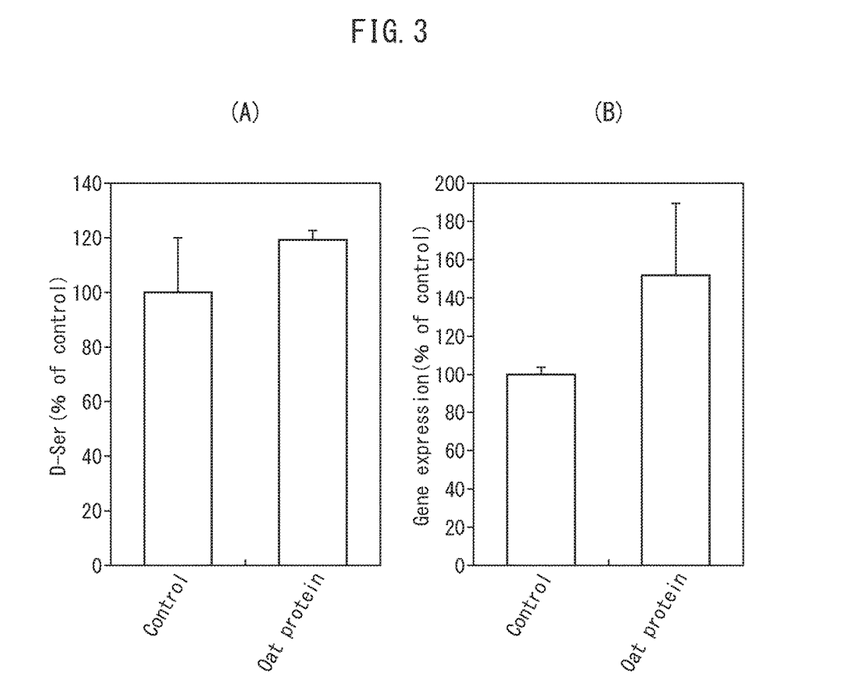
FIG. 3A is a graph showing increase in free D-serine levels by hydrolyzed oat protein solution, which is one of candidate drugs.
FIG. 3B is a graph showing increase in serine racemase expression by hydrolyzed oat protein solution, which is one of candidate drugs.

After rinsing cells with PBS, 500 μL of a 5% trichloroacetic acid aqueous solution was added, the cells were thoroughly dispersed and recovered, and ultrasonic treatment was performed for 30 minutes on ice, after which centrifugal separation was performed to obtain a supernatant. The amino acids in the supernatant were extracted by addition of a 20-fold amount of methanol. The optical isomers of the extracted amino acids were analyzed by a reported method (reference: Yurika Miyoshi et al., Journal of Chromatography B, 877 (2009) 2506-2512). The results are summarized below. The extracted amino acids were subjected to fluorescent derivatization with 4-fluoro-7-nitro-2,1,3-benzooxadiazole (NBD-F) in a borate buffer (pH 8.0). After this derivatization, pH of the solution was adjusted to acidic conditions by adding trifluoroacetic acid. The derivatives were subjected to two-dimensional Micro HPLC (Shiseido Corp.). For the first dimension there was used a micro monolithic ODS column (inner diameter: 0.53 mm, full length: 750 mm, Shiseido Corp.), and for the second dimensional optical resolution, there was used an optical resolution enantio-selective column (inner diameter: 1.5 mm, full length: 250 mm, mobile phase conditions were optimized for each amino acid). The NBD-amino acids were detected by fluorescence at 530 nm (excitation wavelength of 470 nm). The results are shown in Table 2 and FIG. 3A below.

Quantitative PCR (RT-PCR)

After rinsing cells with PBS, MagNA Pure LC (Roche Diagnostic Corp.) was used to extract the mRNA from the cells. Next, a reverse transcriptase SuperScriptVILO (Invitrogen Corp.) kit was used to synthesize cDNA. The cDNA was used as template for real-time PCR using fluorescent dye CyberGreen with a LightCycler (Roche Diagnostic Corp.). The PCR reaction was enzyme activation at 95° C. for 10 minutes followed by amplification reaction at 95° C. for 15 seconds, 60° C. for 10 seconds and 72° C. for 10 seconds, repeated 30 times. The gene expression level was calculated as a relative value from the number of cycles until a unit PCR product was obtained. RT-PCR was conducted with the G3PDH (glyceraldehyde-3-phosphate) gene as the internal standard in addition to the serine racemase gene, and the drug evaluation was conducted by correlating the relative expression level of serine racemase with the relative expression level of G3PDH. The primers selected for use in RT-PCR were those described in NPL 3 and NPL 4. The results are shown in Table 2 and FIG. 3B below.

TABLE 2

| SR expression/ G3PDH | PCR results | | | | | |
| --- | --- | --- | --- | --- | --- | --- |
| | SR | | | D-Serine content | | |
| | SR expression (% control L-Ser(+)) | SR expression SD (% control L-Ser(+)) | p value (VS control) Student's t | SR content (% control L-Ser(+)) | SR content SD (% control L-Ser(+)) | p value (VS control) Student's t |
| Control | 100.00 | 3.50 | | 100.00 | 19.40 | |
| Oat protein | 151.94 | 37.30 | 0.074 | 119.09 | 3.43 | 0.063 |

Of the candidate drugs supplied for this screening, the hydrolyzed oat protein solution promoted serine racemase expression in differentiation-induced keratinocytes. It was also shown that hydrolyzed oat protein solution increases the D-serine content in differentiation-induced keratinocytes. Based on these results, hydrolyzed oat protein solution can be selected as an effective drug for enhancing skin barrier function.

Example 4

Screening of Candidate Drugs

Cell Culturing and Drug Preparation

Normal human keratinocytes were seeded in a 24 well multiplate to a cell density of $2.5 \times 10^4$ cells/well, and cultured in KGM culture medium (Kurabo Industries, Ltd.) under conditions of 37° C., 5% $CO_2$. After 3 days, the medium was exchanged with KGM culture medium containing 1.8 mM calcium chloride, 10 mM L-serine and the candidate drug diluted solution, and culturing was continued for another 2 days. 12 drugs were used as candidate drugs, in which 0.5% Lempuyang extract and 0.5% *Elephantopus mollis* extract were included.

Quantitative PCR (RT-PCR)

After rinsing cells with PBS, MagNA Pure LC(Roche Diagnostic Corp.) was used to extract the mRNA from the cells. Next, a reverse transcriptase SuperScriptVILO (Invitrogen Corp.) kit was used to synthesize cDNA. The cDNA was used as template for real-time PCR using fluorescent dye CyberGreen with a LightCycler (Roche Diagnostic Corp.). The PCR reaction was enzyme activation at 95° C. for 10 minutes followed by amplification reaction at 95° C. for 15 seconds, 60° C. for 10 seconds and 72° C. for 10 seconds, repeated 30 times. The gene expression level was calculated as a relative value from the number of cycles until a unit PCR product was obtained. RT-PCR was conducted with the G3PDH (glyceraldehyde-3-phosphate) gene as the internal standard in addition to the serine racemase gene, and the drug evaluation was conducted by correlating the relative expression level of serine racemase with the relative expression level of G3PDH. The primers selected for use in RT-PCR were those described in NPL 3 and NPL 4. The results are shown in Table 3 below.

TABLE 3

| Serine Racemase expression/ G3PDH | PCR results | | |
| --- | --- | --- | --- |
| | Serine Racemase expression (% control L-Ser(+)) | Serine Racemase expression SD (% control L-Ser(+)) | p value (VS control) Student's t |
| Control | 100.00 | 36.50 | |
| Lempuyang extract | 170.02 | 36.18 | 0.068 |
| *Elephantopus mollis* extract | 173.07 | 15.90 | 0.011 |

Of the candidate drugs supplied for this screening, Lempuyang extract and *Elephantopus mollis* extract promoted serine racemase expression in differentiation-induced keratinocytes. Based on this result, Lempuyang extract and *Elephantopus mollis* extract can be selected as an effective drug for enhancing skin barrier function.

Example 5

Screening Candidate Drugs

Cell Culture and Drug Treatment

Human normal keratinocytes were seeded on 24 well-multiplate at $2.5 \times 10^4$ cells/well of cell density, and was cultured in KGM medium (Kurabo), at 37° C. under 5% $CO_2$ atmosphere. After three days were passed, a medium was exchanged with KGM medium containing 1.8 mM calcium chloride and a diluent of pyridoxal phosphoric acid (PLP) as a candidate drug, and cells were cultured for two days.

Sample Preparation for HPLC and Analysis of Free D-serine by HPLC

Figure 4:
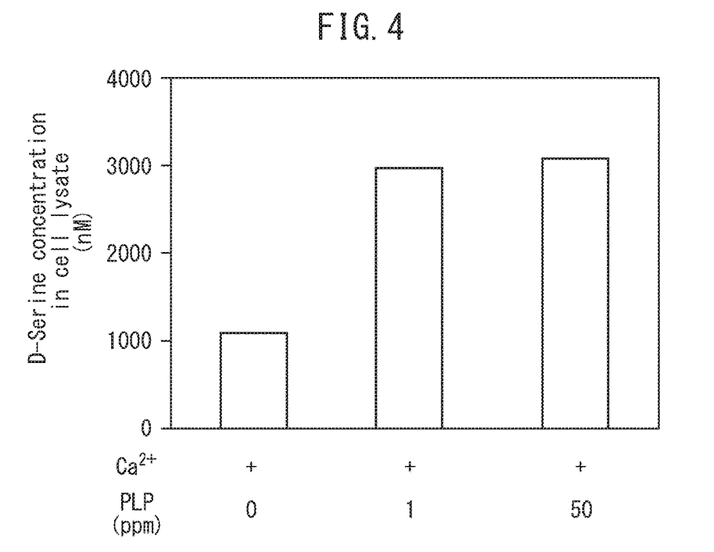
FIG. 4 is a graph showing that free D-serine is increased by adding pyridoxal phosphoric acid (PLP), which is one of candidate drugs, to keratinocytes.

Cells cultured in pyridoxal phosphoric acid added media was washed with PBS, and was suspended by adding 500 μl of 5% trichloro acetic acid solution, and treated with sonication for 30 min, and then centrifugatio is carried out to obtain supernatant. To the supernatant, 20 times amount of methanol was added, and then amino acids were extracted. Enantiomers of the extracted amino acids were analyzed in accordance with the reported method (see Yurika Miyoshi et al, Journal of Chromatography B, 877 (2009) 2506-2512). Overview of the method is shown below. Extracted amino acids were subjected to fluorescent derivatiztion by means of 4-fluoro-7-nitro-2,1,3-benzoxydiazol (NBD-F) in borate buffer (pH 8.0), and then was subject to acidic condition with trifluoro acetic acid. After that it was subjected to two-dimension micro HPLC (Shiseido). For the first dimension, micromonolith ODS column (inner diameter: 0.53 mm, whole length: 750 mm, Shiseido) was used, and then an optic resolution column having 1.5 mm of inner diameter which was suited for optical resolution of each amino acid in the second dimension. NBD-amino acids were determined by detecting fluorescent luminescence (excitation wavelength: 470 nm) at 530 nm. The result of the concentration of D-serine was shown in following FIG. 4. PLP which is a coenzyme of serine racemase is an agent being capable to activate serine racemase, and being capable of enhancing skin barrier function through the activation of serine racemase.

Example 6

The Effect of D-serine on Skin

Three Dimension Culture of Keratinocytes

Human normal keratinocytes were seeded on polycarbonate insert (Millipore) having 12 mm of diameter and 0.4 μm of bore diameter. Then, Human normal keratinocytes were cultured for three days under 5% $CO_2$ atmosphere at 37° C. by adding Cnt-Prime, Epithelial Culture Medium (CELLnTEC Advanced Cell Systems AG) inside and outside of the insert, followed by being cultured for 24 hours by substituting with Cnt-prime 3D Barrier medium (CELLnTEC Advanced Cell Systems AG). Then, medium inside of the insert was discarded, and medium containing D-Ser at 100 μM concentration or Cnt-prime 3D Barrier medium to which D-Ser was not added as a control was added to the outside of the insert, and then cell culture was carried on by allowing the cell surface being exposed to air. After culturing cells for 7 days by substituting medium once in two days, a membrane in the insert was excited with a surgical knife, and was immersed in Trizol reagent (Invitrogen) to extract total RNA.

Gene Expression Analysis by Real-time PCR Method

Total RNA extracted by means of Trizol reagent (Invitrogen) was subjected to NanoDrop 1000 Spectrophotometer (Thermo Fisher Scientific) to determine RNA concentration, and then was converted to cDNA by using SuperScriptVILO (Invitrogen). Relative expression amount of genes of fillagrin (FLG), cornuline (CRNN) and repetin (RPTN), and mitochondrial ribosome protein L19 (MRPL19) which was used as an internal control gene was determined. The following primers are used:

TABLE 4

| Name | Sequence | SEQ ID No. |
|---|---|---|
| FLG-forward | 5'-GGCTCCTTCAGGCTACATTCTA-3' | 1 |
| FLG-reverse | 5'-ATCTGGATTCTTCAGGATTTGC-3' | 2 |
| CRNN-forward | 5'-CAACTGCACAGCGCTCAC-3' | 3 |
| CRNN-reverse | 5'-CAACTGCACAGCGCTCAC-3' | 4 |
| RPTN-forward | 5'-GCTCTTGGCTGAGTTTGGAG-3' | 5 |
| RPTN-reverse | 5'-AGGTTCAAGATGGTTTCCACA-3' | 6 |
| MRPL19-forward) | 5'-GGGATTTGCATTCAGAGATCAG-3' | 7 |
| MRPL19-reverse | 5'-GGAAGGGCATCTCGTAAG-3' | 8 |

Figure 5:
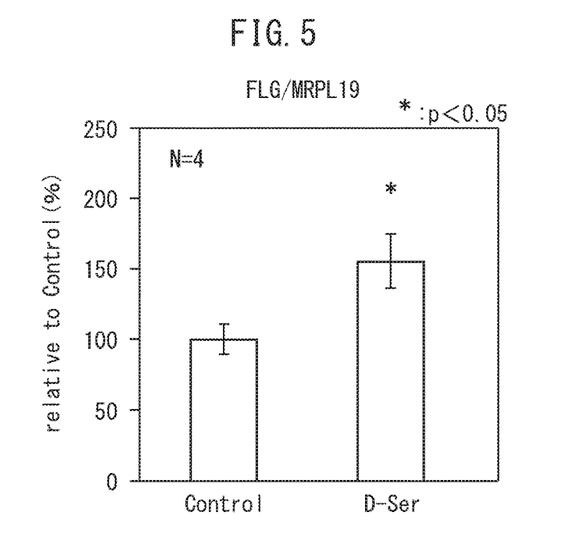
FIG. 5 is a graph showing that D-serine increases the expression level of fillagrin gene in a 3D skin model.
Figure 6:
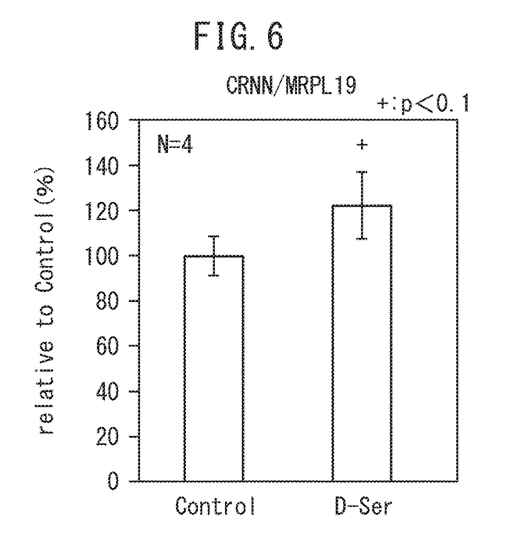
FIG. 6 is a graph showing that D-serine increases the expression level of cornuline gene in a 3D skin model.
Figure 7:
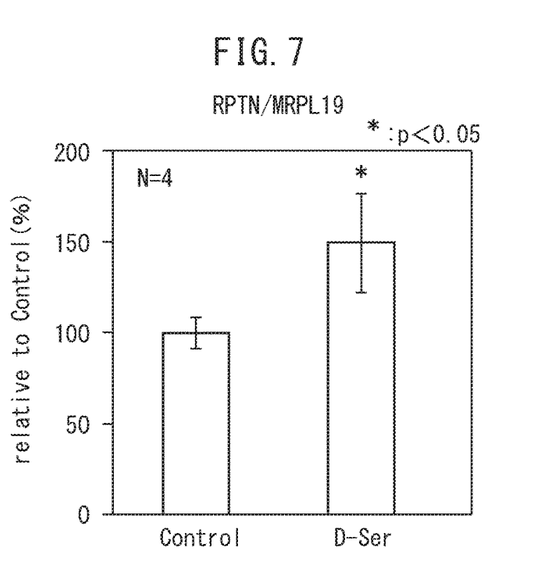
FIG. 7 is a graph showing that D-serine increases the expression level of repetin gene in a 3D skin model.

Relative expression amount of the target gene of each group was determined by means of correction using the expression amount of mitocondrial ribosome protein L19 gene (MRPL19) as an internal control (FIGS. 5-7). Gene expression of these genes was increased by adding D-Ser.

What is claimed is:

1. A method for evaluating a skin barrier function comprising:
   measuring in a skin sample isolated from a subject an expression level of serine racemase; and
   determining the skin barrier function of the subject from the measured expression level of serine racemase.

2. The method of claim 1, wherein said measuring the expression level of serine racemase comprises measuring an amount of serine racemase mRNA in the skin sample.

3. The method of claim 1, wherein said measuring the expression level of serine racemase comprises measuring an amount of serine racemase protein in the skin sample.

4. A method for evaluating a skin barrier function comprising: measuring in a skin sample isolated from a subject an activity of serine racemase and determining the skin barrier function of the subject based on the measured activity of serine racemase.

5. The method of claim 4, wherein said measuring the activity of serine racemase comprises measuring a substrate conversion efficiency by serine racemase in the skin sample.

6. The method of claim 4, wherein said measuring the activity of serine racemase comprises measuring an amount of D-amino acid product in the skin sample.

7. A method for evaluating a skin barrier function comprising: measuring in a skin sample isolated from a subject a D-serine level and determining the skin barrier function of the subject based on the measured D-serine level.

* * * * *

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ggctccttca ggctacattc ta                                               22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
atctggattc ttcaggattt gc                                               22

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
caactgcaca gcgctcac                                                    18
```

```
<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
caactgcaca gcgctcac                                                      18

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gctcttggct gagtttggag                                                    20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
aggttcaaga tggtttccac a                                                  21

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gggatttgca ttcagagatc ag                                                 22

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ggaagggcat ctcgtaag                                                      18
```